United States Patent
Mizumoto et al.

(10) Patent No.: US 8,641,988 B2
(45) Date of Patent: Feb. 4, 2014

(54) SAMPLE ANALYZER AND SAMPLE ANALYSIS SYSTEM

(71) Applicants: Sysmex Corporation, Kobe (JP); Arkray, Inc., Kyoto (JP)

(72) Inventors: Toru Mizumoto, Hyogo (JP); Takayoshi Izumi, Hyogo (JP); Keisuke Tsutsumida, Hyogo (JP); Shinya Nakajima, Kyoto (JP)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 13/629,081

(22) Filed: Sep. 27, 2012

(65) Prior Publication Data

US 2013/0022499 A1  Jan. 24, 2013

Related U.S. Application Data

(63) Continuation of application No. PCT/JP2011/057765, filed on Mar. 29, 2011.

(30) Foreign Application Priority Data

Mar. 30, 2010 (JP) ................................ 2010-076525
May 31, 2010 (JP) ................................ 2010-125142

(51) Int. Cl.
*B01L 99/00* (2010.01)
(52) U.S. Cl.
USPC ................ 422/537; 422/64; 422/65; 422/66; 422/67; 422/536; 436/180; 700/90; 700/91
(58) Field of Classification Search
USPC ........... 422/64–67, 536; 436/180; 700/90–91
See application file for complete search history.

(56) References Cited

U.S. PATENT DOCUMENTS

2005/0070019 A1* 3/2005 Yamamoto ...................... 436/43
2006/0216199 A1* 9/2006 Koike .............................. 422/65
2011/0000763 A1  1/2011 Kimura et al.

FOREIGN PATENT DOCUMENTS

| JP | 58-144753 A | 8/1983 |
| JP | 59-170771 A | 9/1984 |
| JP | 03-279863 A | 12/1991 |
| JP | 06-102272 A | 4/1994 |
| JP | 06-138120 A | 5/1994 |
| JP | 07-049346 A | 2/1995 |
| JP | 09-243645 A | 9/1997 |

(Continued)

OTHER PUBLICATIONS

International Search Report for International Application No. PCT/JP2011/057765, dated Jun. 14, 2011, 2 pages.

(Continued)

*Primary Examiner* — Jyoti Nagpaul
(74) *Attorney, Agent, or Firm* — Brinks Gilson & Lione

(57) ABSTRACT

A sample analyzer which transports a rack holding a plurality of sample containers and analyzes samples includes: a first measurement apparatus which measures samples; a second measurement apparatus which is arranged downstream, in a transport direction, from the first measurement apparatus, and which measures samples; and a transporting apparatus which transports samples to a first supply position for supplying a sample to the first measurement apparatus, and to a second supply position for supplying a sample to the second measurement apparatus. The transporting apparatus linearly transports a rack from the first supply position to the second supply position, and the distance between the first supply position and the second supply position is a multiple of the distance between adjacent sample containers held in the rack.

13 Claims, 13 Drawing Sheets

(56) References Cited

FOREIGN PATENT DOCUMENTS

| | | |
|---|---|---|
| JP | 09-329597 A | 12/1997 |
| JP | 10-300756 A | 11/1998 |
| WO | WO 2009/107817 A1 | 9/2009 |

OTHER PUBLICATIONS

International Preliminary Report on Patentability for International Application No. PCT/JP2011/057765, dated Nov. 13, 2012, 6 pages.

* cited by examiner

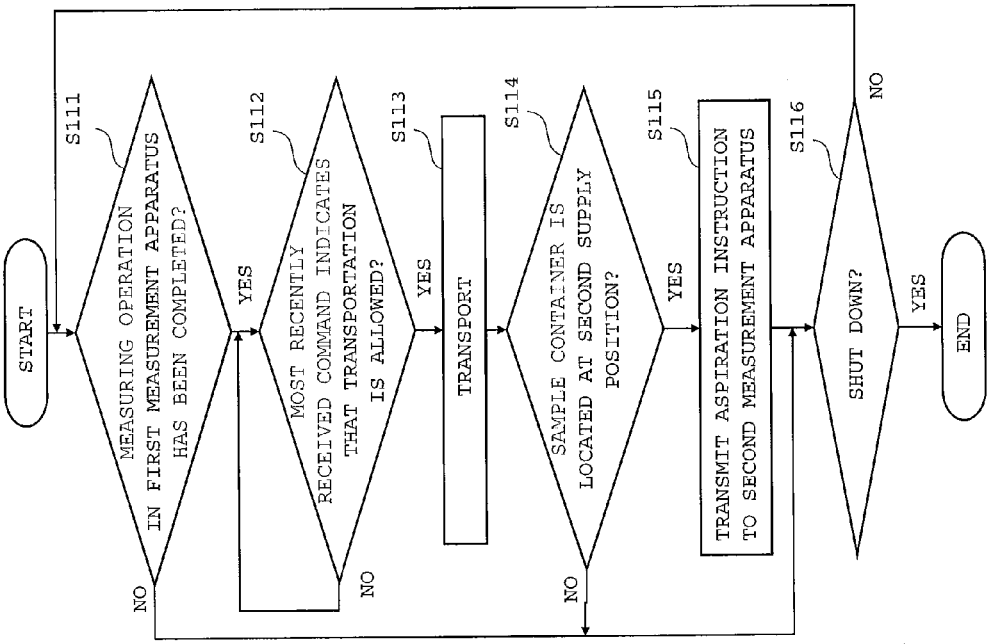
FIG. 6A  MEASUREMENT PROCESS PERFORMED BY FIRST MEASUREMENT APPARATUS
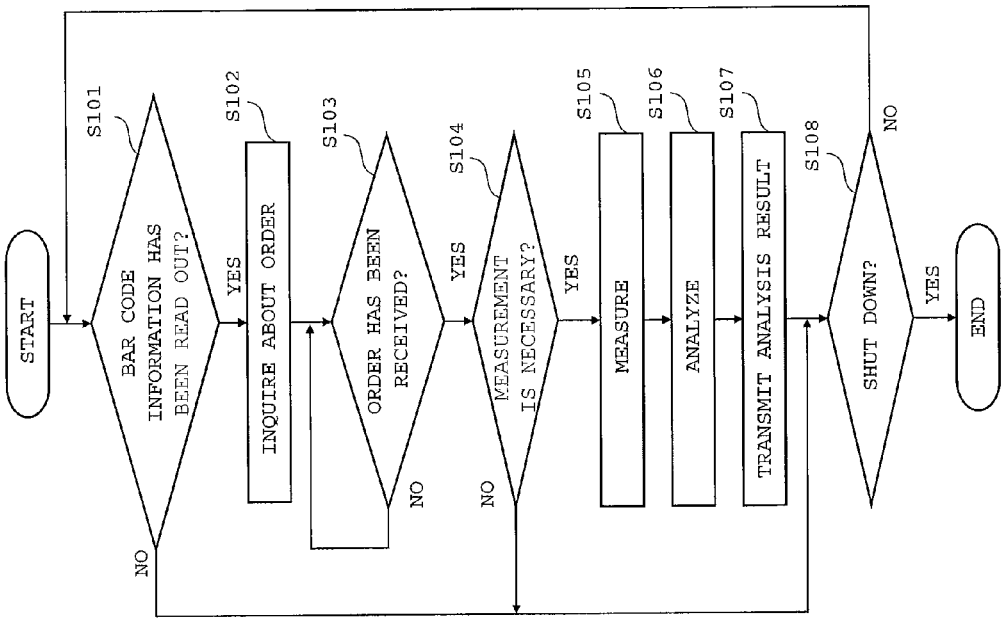
FIG. 6B  TRANSPORT PROCESS PERFORMED BY FIRST MEASUREMENT APPARATUS

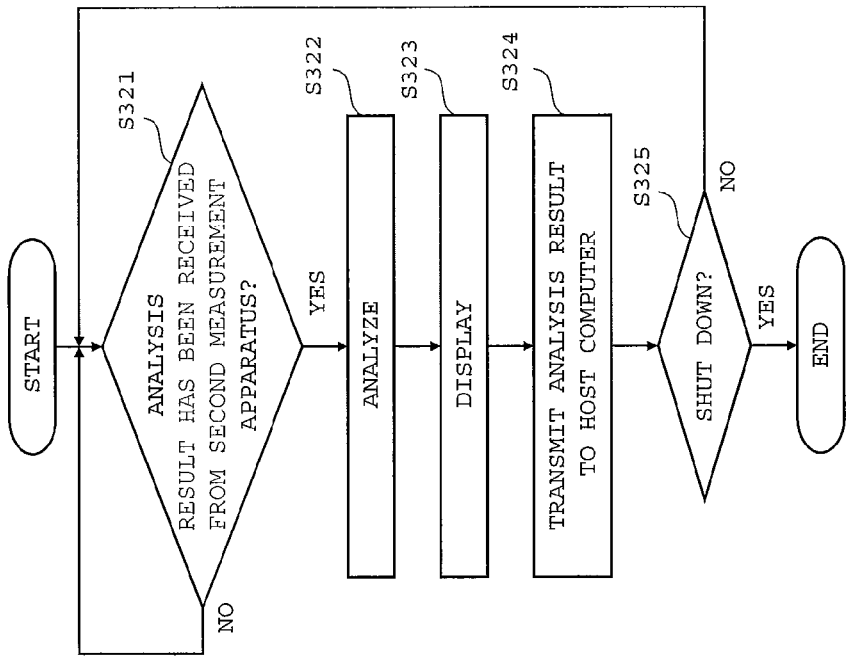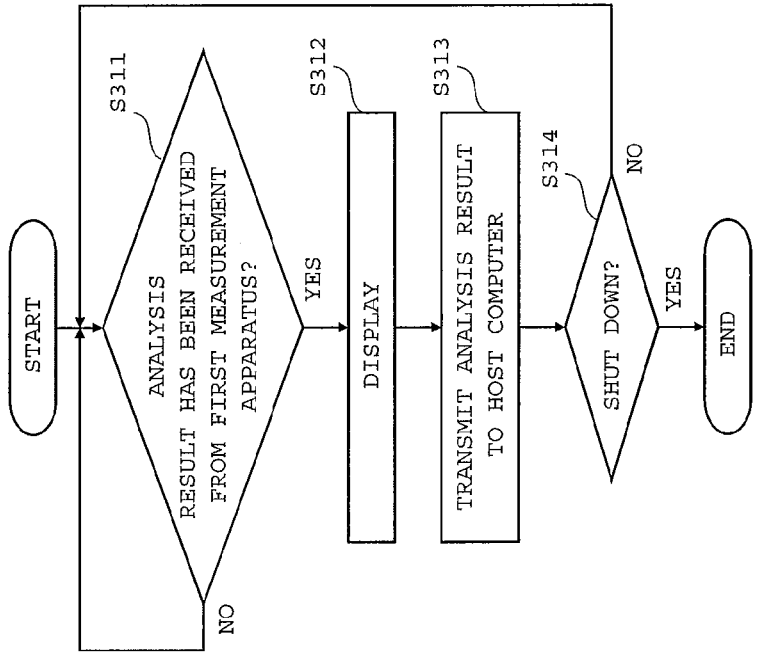

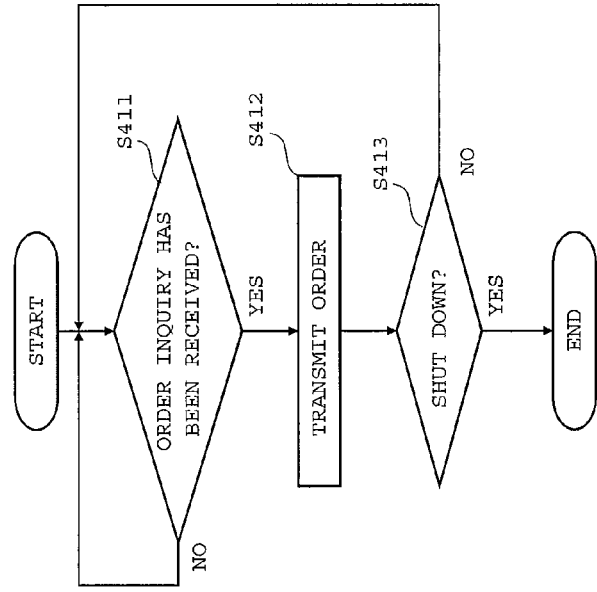
FIG.10B  ORDER REPLY PROCESS PERFORMED BY HOST COMPUTER
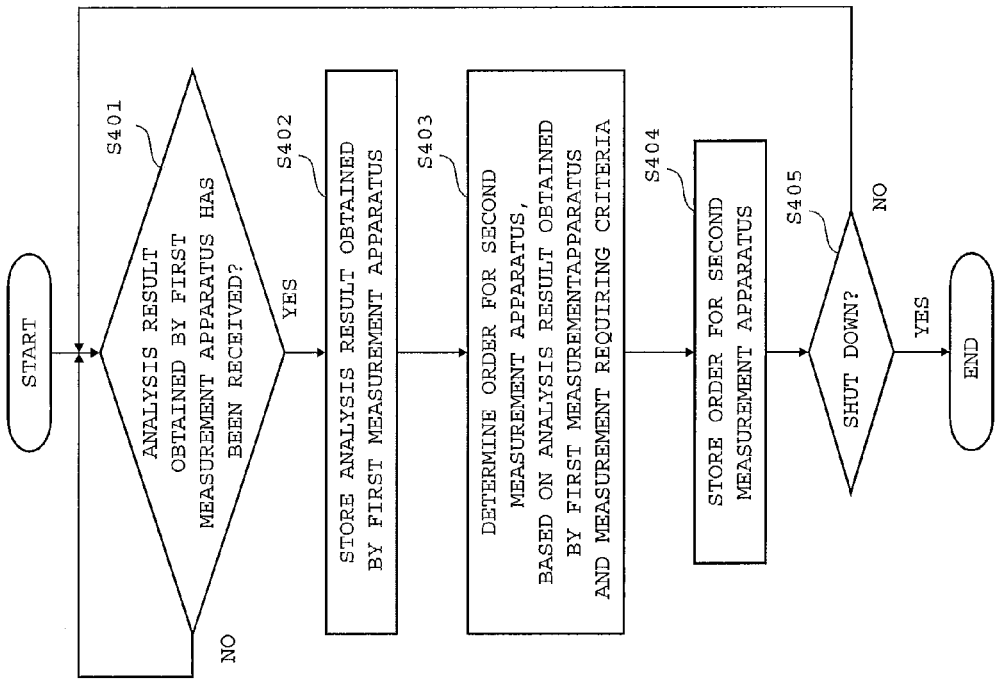
FIG.10A  ORDER DETERMINATION PROCESS PERFORMED BY HOST COMPUTER

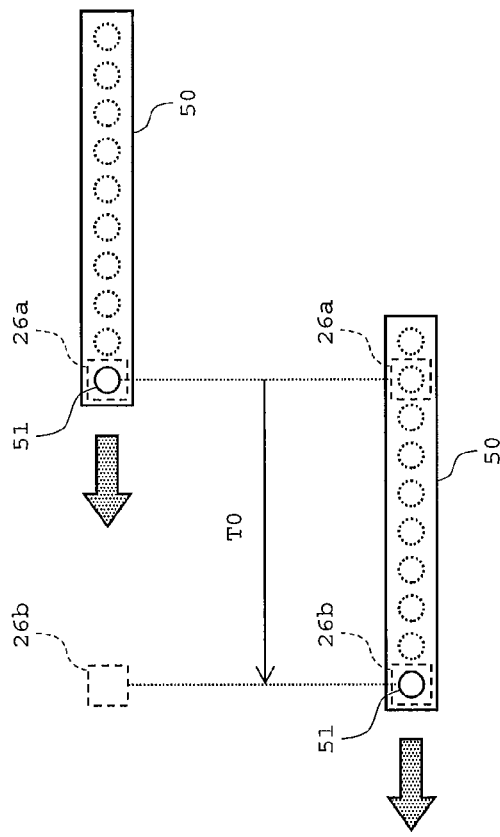
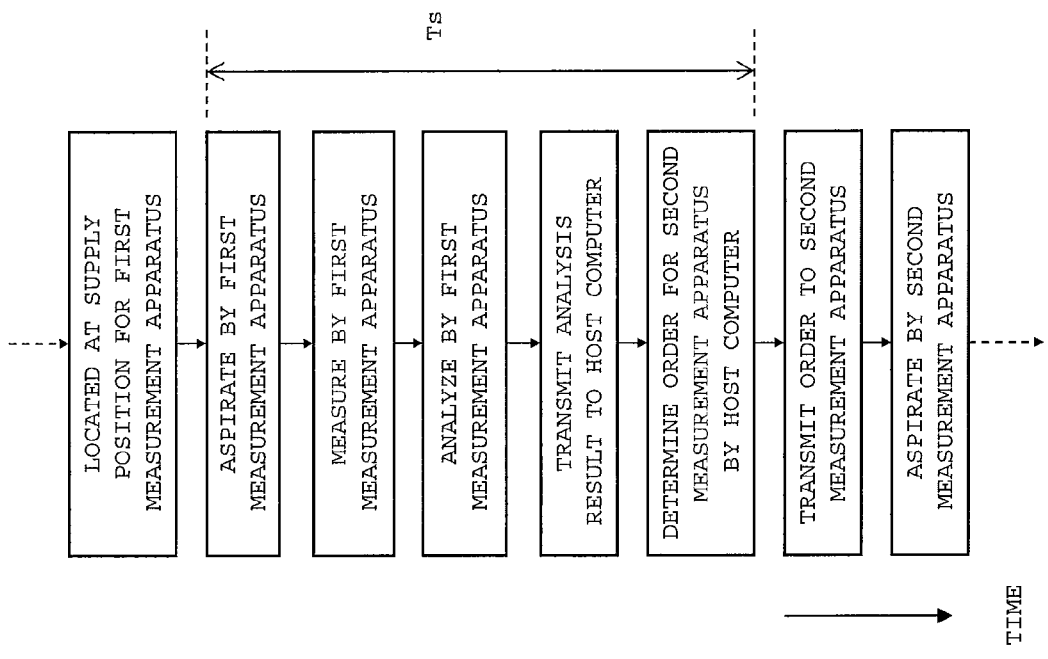

SAMPLE ANALYZER AND SAMPLE ANALYSIS SYSTEM

RELATED APPLICATIONS

This application is a continuation of PCT/JP2011/057765 filed on Mar. 29, 2011, which claims priority to Japanese Application Nos. 2010-076525 filed on Mar. 30, 2010 and 2010-125142 filed on May 31, 2010. The entire contents of these applications are incorporated herein by reference.

BACKGROUND OF THE INVENTION

1. Field of the Invention

The present invention relates to sample analyzers and sample analysis systems which perform predetermined processes such as tests and analyses onto samples such as urine and blood.

2. Description of Related Art

Sample analysis systems which each include a plurality of analyzers and a transporting apparatus which transports samples to the plurality of analyzers are known.

As such a sample analysis system, for example, Patent Literature 1 (Japanese Laid-Open Patent Publication No. H7-49346) discloses a urinary sediment testing system which includes a urine component testing apparatus, a urinary sediment testing apparatus, and a specimen transporting apparatus which linearly transports samples to these apparatuses. The urine component testing apparatus and the urinary sediment testing apparatus perform processes on samples located at predetermined positions on the specimen transporting apparatus, respectively.

In the urinary sediment testing system described in Patent Literature 1, the sample processed at a predetermined position on the specimen transporting apparatus by the urine component testing apparatus is transported on the transporting apparatus, and then processed at a predetermined position on the specimen transporting apparatus by the urinary sediment testing apparatus which is arranged on the downstream side. In this case, if while sample processing is being performed by the upstream urine component testing apparatus, another sample can be simultaneously processed by the downstream urinary sediment testing apparatus, processing of samples can be efficiently performed. However, Patent Literature 1 discloses no configuration for that.

SUMMARY OF THE INVENTION

A first aspect of the present invention relates to a sample analyzer which transports a rack holding a plurality of sample containers and analyzes samples. The sample analyzer according to the present aspect includes: a first measurement apparatus which measures samples; a second measurement apparatus which is arranged downstream, in a transport direction, from the first measurement apparatus, and which measures samples; and a transporting apparatus which transports samples to a first supply position for supplying a sample to the first measurement apparatus, and to a second supply position for supplying a sample to the second measurement apparatus. Here, the transporting apparatus linearly transports a rack from the first supply position to the second supply position, and a distance between the first supply position and the second supply position is a multiple of a distance between adjacent sample containers held in the rack.

In the sample analyzer according to the present aspect, the distance between the first supply position and the second supply position is a multiple of the distance between adjacent sample containers held in a rack. Accordingly, when one sample is transported to the first supply position, another sample can be concurrently located at the second supply position. Therefore, it is possible to simultaneously process two samples, and thus, it is possible to efficiently perform processing of samples.

A second aspect of the present invention relates to a sample analysis system. The sample analysis system according to the present aspect includes: a sample analyzer which transports a rack holding a plurality of sample containers and analyzes samples; and a computer communicable to the sample analyzer. The sample analyzer includes: a first measurement apparatus which measures samples; a second measurement apparatus which is arranged downstream, in a transport direction, from the first measurement apparatus, and which measures samples; and a transporting apparatus which transports samples to a first supply position for supplying a sample to the first measurement apparatus, and to a second supply position for supplying a sample to the second measurement apparatus. Here, the transporting apparatus linearly transports a rack from the first supply position to the second supply position, and a distance between the first supply position and the second supply position is a multiple of a distance between adjacent sample containers held in the rack. The computer includes determination section which determines, based on a measurement result obtained by the first measurement apparatus, whether measurement by the second measurement apparatus is necessary. In the sample analysis system according to the present aspect, it is possible to efficiently perform processing of samples, as in the sample analyzer according to the first aspect.

It should be noted that, in the above aspects, "a distance between the first supply position and the second supply position is a multiple of a distance between adjacent sample containers held in the rack" does not mean that the distance between the first supply position and the second supply position is exactly a multiple of the distance between adjacent sample containers held in the rack. Even when the distance between the first supply position and the second supply position does not exactly agree with a multiple of the distance between adjacent sample containers held in the rack, due to an error in the size of the rack or the sample containers, and the like, if two samples can be simultaneously processed at the first supply position and the second supply position, it is covered by the concept "a distance between the first supply position and the second supply position is a multiple of a distance between adjacent sample containers held in the rack."

A third aspect of the present invention relates to a sample analyzer which transports a rack holding a plurality of sample containers and analyzes samples. The sample analyzer according to the present aspect includes: a first measurement apparatus which measures samples; a second measurement apparatus which is arranged downstream, in a transport direction, from the first measurement apparatus, and which measures samples; and a transporting apparatus which transports samples to a first supply position for supplying a sample to the first measurement apparatus, and to a second supply position for supplying a sample to the second measurement apparatus. Here, the transporting apparatus linearly transports a rack from the first supply position to the second supply position, and a distance between the first supply position and the second supply position is shorter than or equal to a distance from a sample container held in one rack at one end thereof to a sample container held in the rack at the other end thereof.

In the sample analyzer according to the present aspect, the distance between the first supply position and the second supply position is shorter than or equal to the distance from a sample container held in one rack at one end thereof to a sample container held in the rack at the other end thereof. Therefore, it is possible to shorten the distance between the first supply position and the second supply position, and thus, it is possible to speedily obtain a measurement result or an analysis result obtained by the second measurement apparatus.

A fourth aspect of the present invention relates to a sample analyzer which transports a rack holding a plurality of sample containers and analyzes samples. The sample analyzer according to the present aspect includes: a first measurement apparatus which measures samples; a second measurement apparatus which is arranged downstream, in a transport direction, from the first measurement apparatus, and which measures samples; and a transporting apparatus which transports samples to a first supply position for supplying a sample to the first measurement apparatus, and to a second supply position for supplying a sample to the second measurement apparatus. Here, the transporting apparatus linearly transports a plurality of racks in a state of being adjacent to each other, from the first supply position to the second supply position, and the transporting apparatus concurrently locates at the first supply position a sample held in a first rack among the plurality of racks, and locates at the second supply position a sample held in a second rack among the plurality of racks which is located downstream, in a transport direction, from the first rack.

In the sample analyzer according to the present aspect, when one sample on the first rack is transported to the first supply position, another sample on the second rack can be concurrently located at the second supply position. Therefore, it is possible to simultaneously process two samples, and thus, it is possible to efficiently perform processing of samples.

BRIEF DESCRIPTION OF THE DRAWINGS

These and other objects, and novel features of the present invention will become more apparent upon reading the following detailed description of the embodiment along with the accompanying drawings.

FIGS. 6A and 6B show flow charts respectively showing a measurement process and a transport process performed by the first measurement apparatus according to an embodiment;

FIGS. 9A and 9B show flow charts respectively showing display processes performed by the information processing apparatus according to an embodiment;

FIGS. 10A and 10B show flow charts respectively showing an order determination process and an order reply process performed by the host computer according to an embodiment;

FIGS. 11A and 11B illustrate how to set the distance between the first supply position and the second supply position according to an embodiment;

It should be noted that the drawings are solely for description and do not limit the scope of the present invention by any degree.

DETAILED DESCRIPTION OF THE PREFERRED EMBODIMENTS

The present embodiment is realized by applying the present invention to a clinical sample analyzer which performs tests (urine qualitative tests) regarding urine protein, urine sugar, and the like, and tests (urinary sediment tests) regarding red blood cells, white blood cells, epithelial cells, and the like contained in urine. A urinary sediment test is performed on a sample for which it has been determined that a urinary sediment test is necessary as a result of a urine qualitative test performed on the sample. In the present embodiment, a plurality of sample containers respectively containing different samples are set in a rack, the rack is set in a sample analyzer, and testing of the samples are performed.

In the embodiment, a host computer 40 corresponds to a "computer" in the claims. A sample rack 50 corresponds to a "rack" in the claims. A CPU 121a, a CPU 301 and a CPU 401a correspond to a "determination section" in the claims. The description regarding the correspondence between the claims and the embodiment is merely an example, and the claims are not limited by the description of the embodiment.

Hereinafter, a sample analyzer according to the present embodiment will be described with reference to the drawings.

Figure 1:
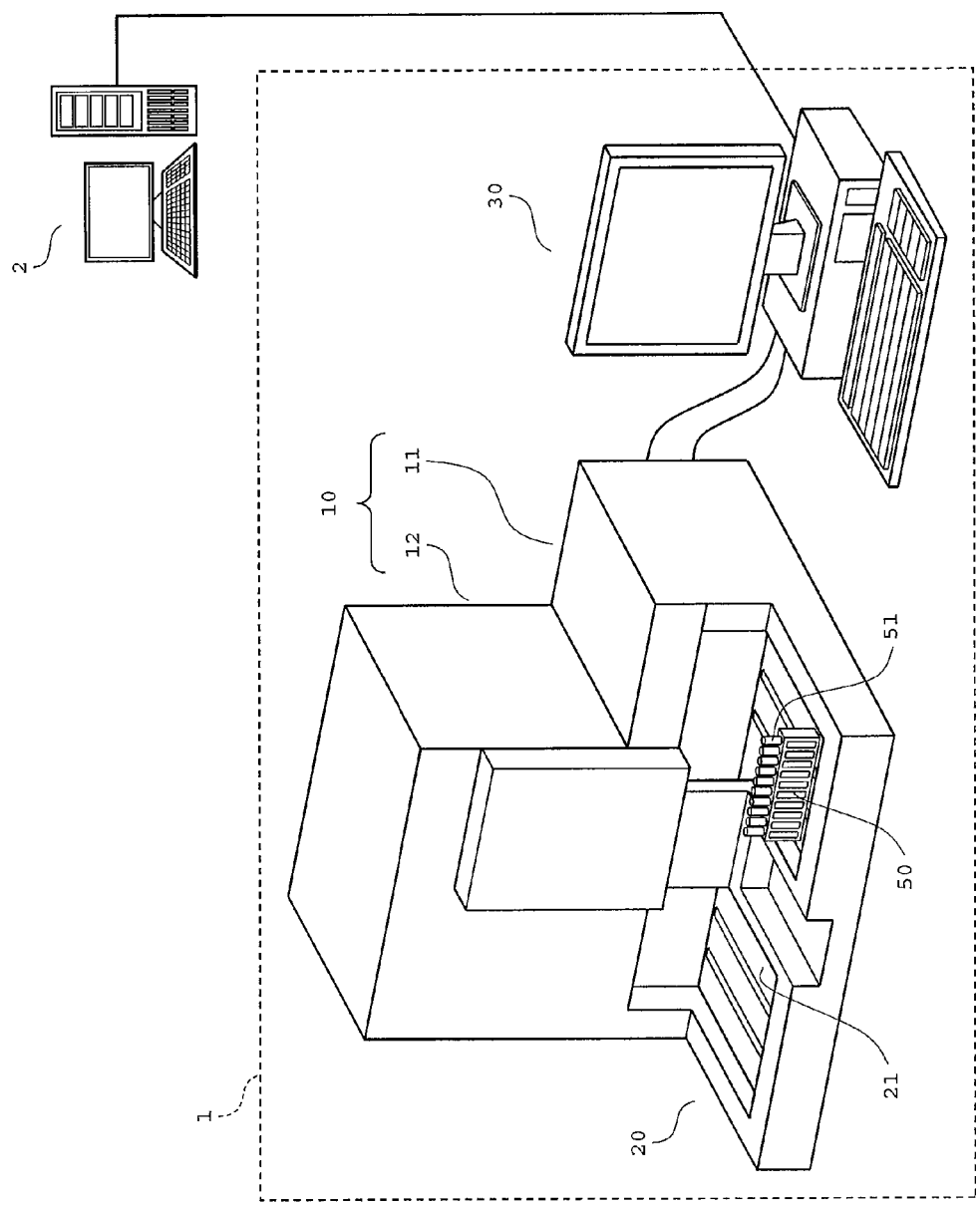
FIG. 1 shows an overall configuration of a system including a sample analyzer according to an embodiment.

FIG. 1 shows an overall configuration of a system including a sample analyzer 1. The sample analyzer 1 according to the present embodiment includes a sample measurement apparatus 10, a transporting apparatus 20, and an information processing apparatus 30.

The sample measurement apparatus 10 includes a first measurement apparatus 11 which performs urine qualitative tests and a second measurement apparatus 12 which performs urinary sediment tests. The first measurement apparatus 11 and the second measurement apparatus 12 are communicably connected to each other. Moreover, the first measurement apparatus 11 and the second measurement apparatus 12 are each communicably connected to the information processing apparatus 30. Further, the first measurement apparatus 11 is communicably connected to the transporting apparatus 20.

The transporting apparatus 20 is a single unit common for the first measurement apparatus 11 and the second measurement apparatus 12. The transporting apparatus 20 is mounted to the front face of the sample measurement apparatus 10 and includes a transport path 21. The transport path 21 has a bottom face of a flat plate shape, provided at a lower level than the upper face of the transporting apparatus 20. In a sample rack 50 which is transported on the transport path 21, ten holders are formed so as to be able to hold ten sample containers 51, respectively. By being held in a holder of the sample rack 50, each sample container 51 is transported on the transport path 21, along with the sample rack 50. A bar code label (not shown) for identifying a sample is affixed to a lateral side of the sample container 51. The information processing apparatus 30 is communicably connected to a host computer 40 via a communication line.

Figure 2:
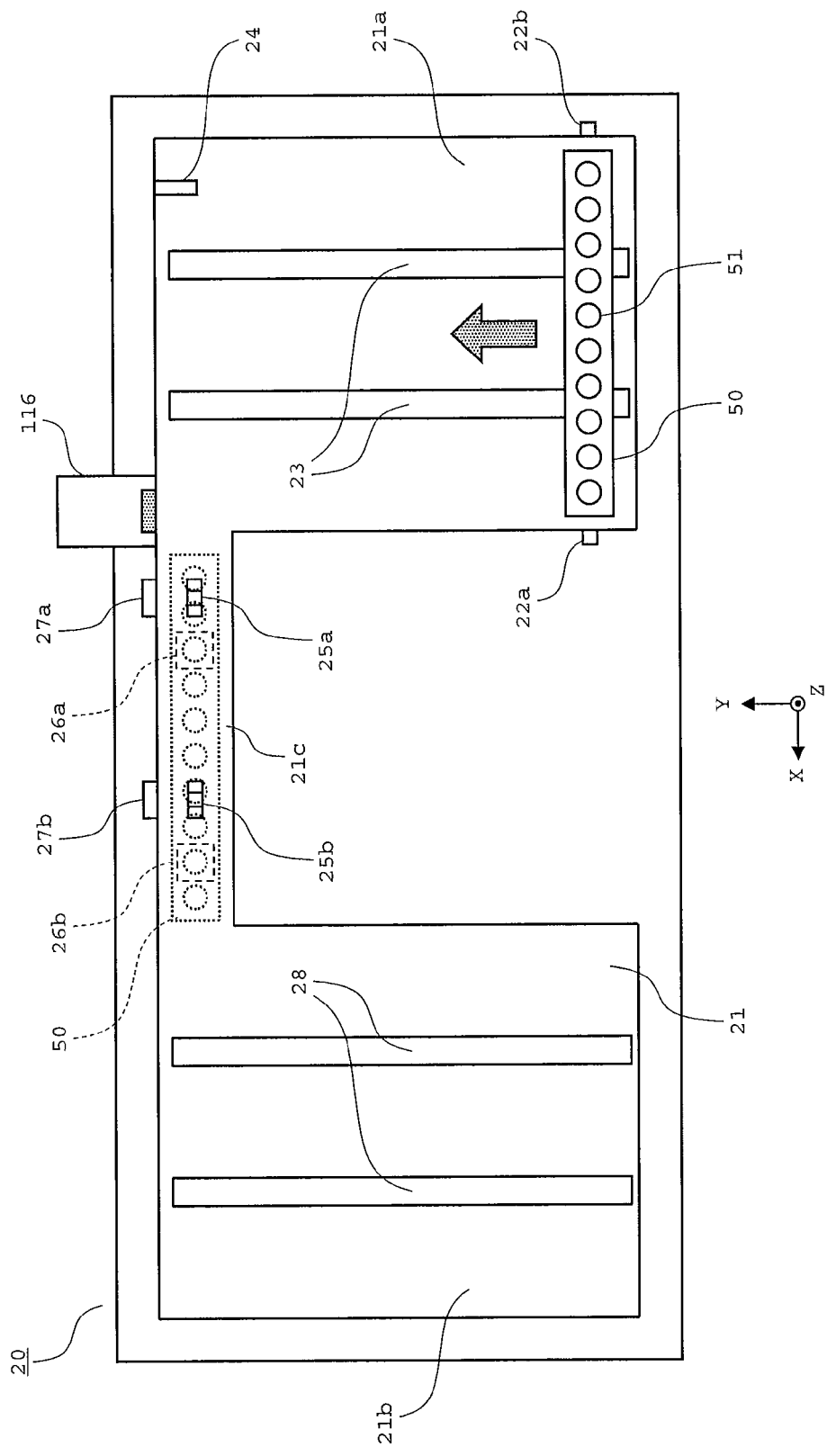
FIG. 2 is a plan view showing a configuration of a transporting apparatus according to an embodiment, viewed from above.

FIG. 2 is a plan view showing a configuration of the transporting apparatus 20, viewed from above.

The transporting apparatus 20 includes the transport path 21, transmissive sensors 22a and 22b, belts 23 and 28, a pushing-out mechanism 24, lateral transportation sensors 25a and 25b, and reflective sensors 27a and 27b. The transport path 21 includes a right vessel region 21a, a left vessel region 21b, and a connection region 21c. The right vessel region 21a and the left vessel region 21b are connected to each other by means of the connection region 21c.

The transmissive sensors 22a and 22b are composed of a light emitter and a light receiver, and detect a sample rack 50 located at the front side in the right vessel region 21a (at the end in the Y-axis negative direction). Based on an output signal from the sensors 22a and 22b, it is detected that a sample rack 50 is placed at the front side in the right vessel region 21a by a user. The belt 23 is provided in the right vessel region 21a, and moves the sample rack 50 placed in the right vessel region 21a in the Y-axis positive direction, to locate it to the rear side in the right vessel region 21a (at the end in the Y-axis positive direction).

The pushing-out mechanism 24 includes a driving section (not shown) further to the rear than the transport path 21, and is configured such that a pushing-out claw moves from the right rear of the right vessel region 21a to the left rear of the left vessel region 21b in the left-right direction (X-axis direction). In FIG. 2, only the claw of the pushing-out mechanism 24 is shown. By the pushing-out mechanism 24 pushing the right-end side face of the sample rack 50, the sample rack 50 located at the rear side of the right vessel region 21a is moved, via the connection region 21c, to the rear side of the left vessel region 21b. As will be described later, a process of transporting the sample rack 50 near the connection region 21c is performed as appropriate, in accordance with measuring operation statuses of the first measurement apparatus 11 and the second measurement apparatus 12.

A bar code reader 116 reads out bar code information from a bar code label affixed to the sample container 51 located in front of (Y-axis negative direction) the bar code reader 116. It should be noted that the bar code reader 116 is controlled by a controller of the first measurement apparatus 11, as described later.

Each of the lateral transportation sensors 25a and 25b has a claw slightly projecting upward (Z-axis positive direction) from the bottom face of the transport path 21 (the connection region 21c). When the sample rack 50 is moved from right to left (X-axis positive direction), the states of the claws of the lateral transportation sensors 25a and 25b change between a projecting state and a non-projecting state relative to the bottom face of the transport path 21, in accordance with opening parts and non-opening parts which are formed in the bottom face of the sample rack 50 at intervals between holders for the sample container 51. Accordingly, it is determined as appropriate whether the distance by which the pushing-out mechanism 24 has been moved agrees with the distance by which the sample rack 50 has been moved.

A first supply position 26a and a second supply position 26b are positions at which samples contained in sample containers 51 are aspirated by the first measurement apparatus 11 and the second measurement apparatus 12, respectively. For example, as shown by the broken line in FIG. 2, a sample rack 50 is located in the connection region 21c. The distance between the first supply position 26a and the second supply position 26b is set to be shorter than or equal to the distance between the sample container 51 held in the holder at the left end (at the end in the X-axis positive direction in FIG. 2) of the sample rack 50 and the sample container 51 held in the holder at the right end (at the end in the X-axis negative direction in FIG. 2). Moreover, the interval between the first supply position 26a and the second supply position 26b is set such that the sample containers 51 held in two different holders of one sample rack 50 are concurrently located at the first supply position 26a and the second supply position 26b, respectively.

FIG. 3 shows the distance between the first supply position 26a and the second supply position 26b. It should be noted that the distances between adjacent sample containers 51 held in the sample rack 50 are all set to d.

Figure 3A:
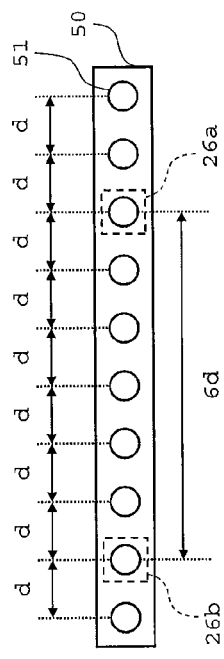
FIGS. 3A-3C show the distance between a first supply position and a second supply position according to an embodiment.

As shown in FIG. 3A, the distance between the first supply position 26a and the second supply position 26b is set to $6d$ in the present embodiment. When the distance between the first supply position 26a and the second supply position 26b is set to a multiple of d, it is possible to concurrently locate sample containers 51 held in two different holders of one sample rack 50, at the first supply position 26a and the second supply position 26b, respectively.

Figure 3B:
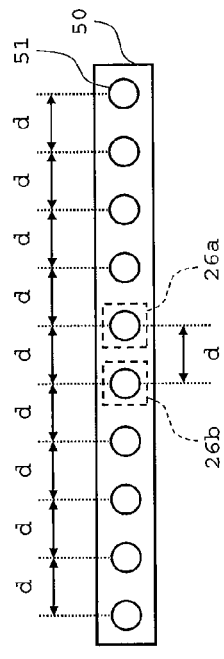
Figure 3C:
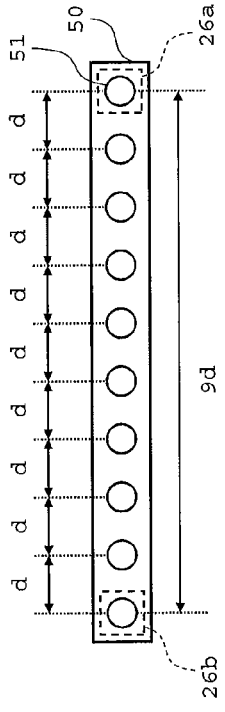

It should be noted that, as shown in FIG. 3B and 3C, the distance between the first supply position 26a and the second supply position 26b may be set, for example, d or $9d$. Also in either case, it is possible to concurrently locate sample containers 51 held in two different holders of one sample rack 50, at the first supply position 26a and the second supply position 26b, respectively.

With reference back to FIG. 2, when measurement is performed by the first measurement apparatus 11, a nozzle (not shown) provided in the first measurement apparatus 11 is inserted into the sample container 51 located at the first supply position 26a. Subsequently, the sample contained in the sample container 51 is aspirated by the nozzle. The aspirated sample is measured in the first measurement apparatus 11. When the aspiration is completed, the nozzle is drawn from the sample container 51, and the sample rack 50 holding this sample container 51 is moved leftward by the pushing-out mechanism 24.

Also when measurement is performed by the second measurement apparatus 12, a nozzle (not shown) provided in the second measurement apparatus 12 is similarly inserted into the sample container 51 located at the second supply position 26b. Subsequently, the sample contained in the sample container 51 is aspirated by the nozzle. The aspirated sample is measured in the second measurement apparatus 12. When the aspiration is completed, the nozzle is drawn from the sample container 51, and the sample rack 50 holding this sample container 51 is moved leftward by the pushing-out mechanism 24.

The reflective sensors 27a and 27b detect whether holders for holding sample containers 51 of the sample rack 50 located in front of (Y-axis negative direction) the reflective sensors 27a and 27b are holding sample containers 51, respectively. Accordingly, it is possible to confirm again whether the sample container 51 whose bar code information was read by the bar code reader 116 is being held in a corresponding holder of the sample rack 50, before aspiration therefore is performed.

The belt 28 is provided in the left vessel region 21b, and moves the sample rack 50 located at the rear side (at the end in the Y-axis positive direction) of the left vessel region 21b, in the Y-axis negative direction, thereby locating it at the front (at the end in the Y-axis negative direction) of the left vessel region 21b. Then, the sample rack 50 located at the front of the left vessel region 21b is taken out by the user.

Figure 4:
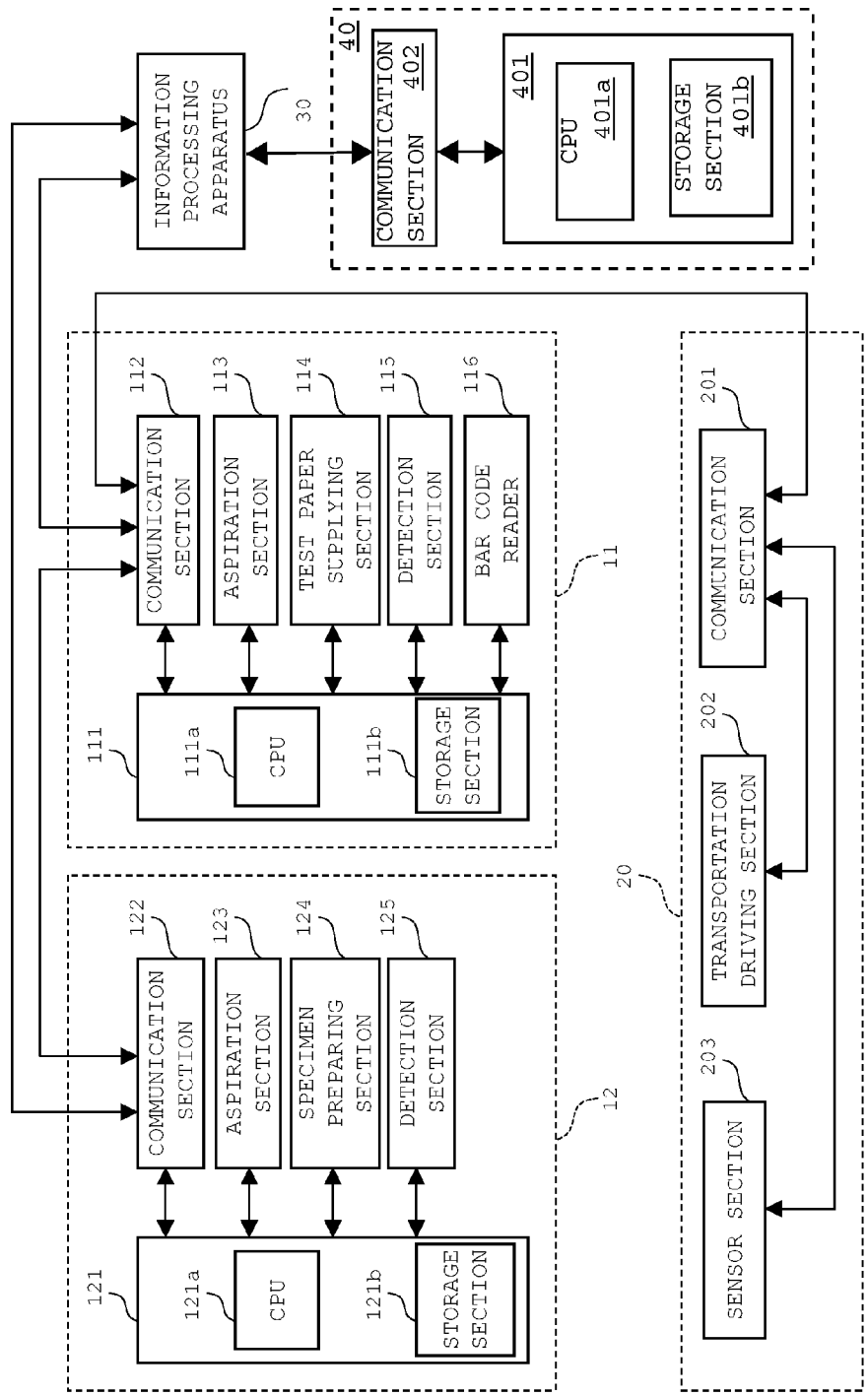
FIG. 4 shows circuit configurations of a first measurement apparatus, a second measurement apparatus, a transporting apparatus, and a host computer according to an embodiment.

FIG. 4 shows circuit configurations of the first measurement apparatus 11, the second measurement apparatus 12, the transporting apparatus 20, and the host computer 40.

The first measurement apparatus 11 includes a controller 111, a communication section 112, an aspiration section 113, a test paper supplying section 114, a detection section 115, and the bar code reader 116. The controller 111 includes a CPU 111a and a storage section 111b. The CPU 111a executes computer programs stored in the storage section 111b and controls sections of the first measurement apparatus 11. Moreover, the CPU 111a controls sections of the transporting apparatus 20 via the communication section 112. The storage section 111b includes storage means such as a ROM, a RAM, and a hard disk.

The communication section 112 processes signals from the controller 111 to output the resultant signals to the second measurement apparatus 12, the transporting apparatus 20, and the information processing apparatus 30, and processes signals from the second measurement apparatus 12, the transporting apparatus 20, and the information processing apparatus 30 to output the resultant signals to the controller 111. The aspiration section 113 aspirates the sample in the sample container 51 located at the first supply position 26a via the nozzle of the first measurement apparatus 11. The test paper supplying section 114 takes out test paper necessary for measurement from a test paper feeder in which test paper is stored, and applies as a spot the sample aspirated by the aspiration section 113 onto the taken-out test paper. The detection section 115 measures the test paper on which the sample has been applied as a spot. A measurement result obtained by the measurement is outputted to the controller 111 and analyzed by the controller 111. The bar code reader 116 reads out bar code information from the bar code label affixed to the sample container 51, and outputs the bar code information to the controller 111.

The second measurement apparatus 12 includes a controller 121, a communication section 122, an aspiration section 123, a specimen preparing section 124, and a detection section 125. The controller 121 includes a CPU 121a and a storage section 121b. The CPU 121a executes computer programs stored in the storage section 121b and controls sections of the second measurement apparatus 12. The storage section 121b includes storage means such as a ROM, a RAM, and a hard disk.

The communication section 122 processes signals from the controller 121 to output the resultant signals to the first measurement apparatus 11 and the information processing apparatus 30, and processes signals from the first measurement apparatus 11 and the information processing apparatus 30 to output the resultant signals to the controller 121. The aspiration section 123 aspirates the sample in the sample container 51 located at the second supply position 26b via the nozzle of the second measurement apparatus 12. The specimen preparing section 124 mixes and stirs the sample aspirated by the aspiration section 123 and a reagent necessary for measurement, to prepare a specimen for measurement to be performed by the detection section 125. The detection section 125 measures the specimen prepared by the specimen preparing section 124. A measurement result obtained by the measurement is outputted to the controller 121.

The transporting apparatus 20 includes a communication section 201, a transportation driving section 202, and a sensor section 203. The communication section 201 processes signals from the first measurement apparatus 11 to output the resultant signals to sections of the transporting apparatus 20, and processes signals from sections of the transporting apparatus 20 to output the resultant signals to the first measurement apparatus 11.

The transportation driving section 202 is controlled by the CPU 111a of the first measurement apparatus 11. It should be noted that the transportation driving section 202 includes the belts 23 and 28 and the pushing-out mechanism 24 shown in FIG. 2. The sensor section 203 outputs output signals from various sensors, to the first measurement apparatus 11 via the communication section 201. It should be noted that the sensor section 203 includes the sensors 22a and 22b, the lateral transportation sensors 25a and 25b, and the sensors 27a and 27b shown in FIG. 2.

The host computer 40 includes a controller 401, and a communication section 402. The controller 401 includes a CPU 401a and a storage section 401b. The CPU 401a executes computer programs stored in the storage section 401b, and when receiving an order inquiry from the information processing apparatus 30, the CPU 401a returns an order stored in the storage section 401b. Moreover, the CPU 401a determines an order for the second measurement apparatus 12, based on an analysis result received from the first measurement apparatus 11 via the information processing apparatus 30 and based on measurement requiring criteria stored in the storage section 401b. The storage section 401b includes storage means such as a ROM, a RAM, and a hard disk.

Figure 5:
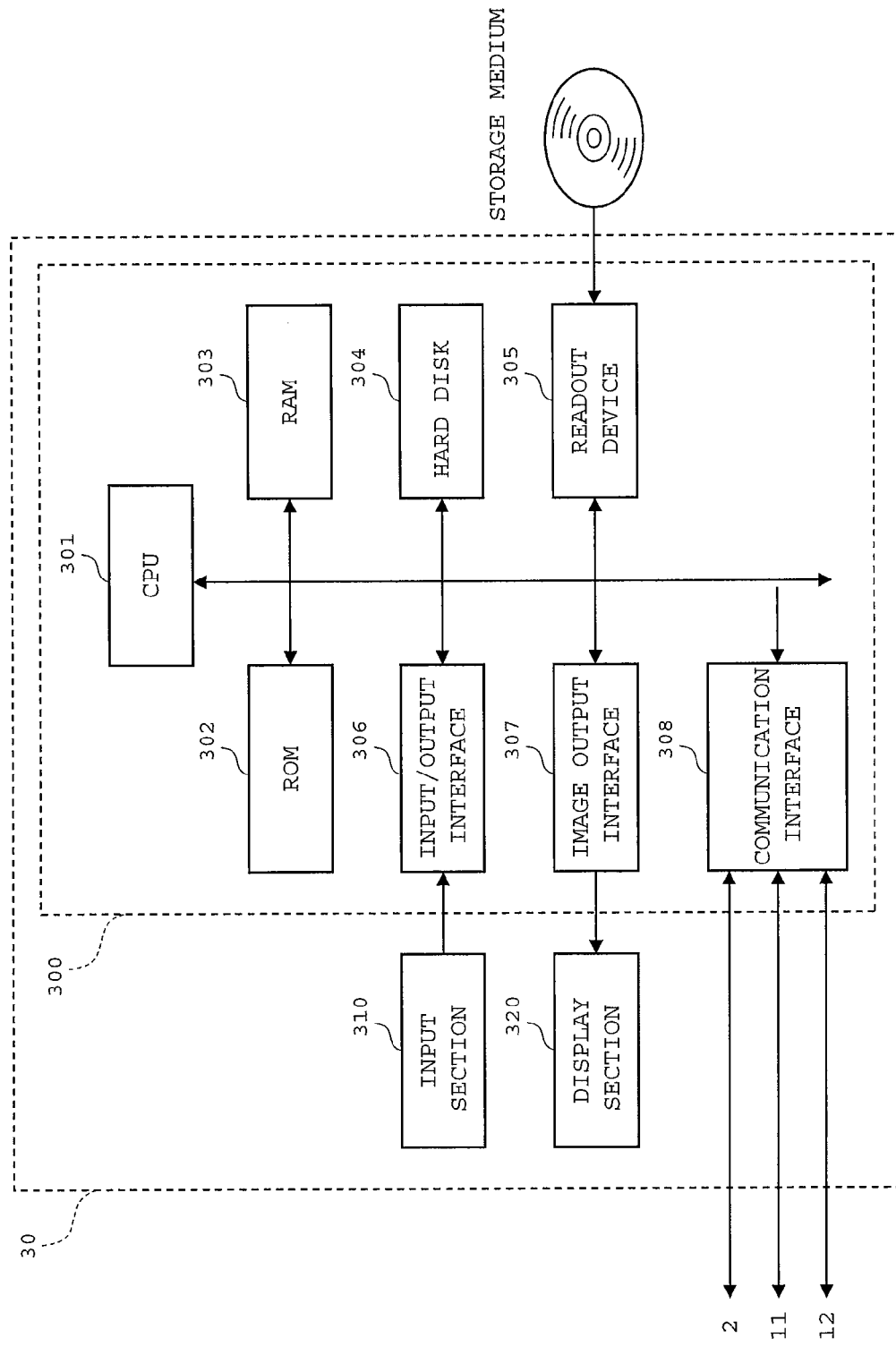
FIG. 5 shows a circuit configuration of an information processing apparatus according to an embodiment.

FIG. 5 shows a circuit configuration of the information processing apparatus 30.

The information processing apparatus 30 is implemented by a personal computer, and includes a body 300, an input section 310, and a display section 320. The body 300 includes a CPU 301, a ROM 302, a RAM 303, a hard disk 304, a readout device 305, an input/output interface 306, an image output interface 307, and a communication interface 308.

The CPU 301 executes computer programs stored in the ROM 302 and computer programs loaded onto the RAM 303. The RAM 303 is used for reading out computer programs stored in the ROM 302 and the hard disk 304. The RAM 303 is also used as a work area for the CPU 301 when the CPU 301 executes these computer programs.

Various computer programs, such as an operating system and application programs, to be executed by the CPU 301, and data used for execution of such computer programs are installed in the hard disk 304. That is, a program for inquiring of the host computer 40 about orders based on later-described order inquiries transmitted from the first measurement apparatus 11 and the second measurement apparatus 12, a program for transmitting orders that have been transmitted from the host computer 40, to the first measurement apparatus 11 and the second measurement apparatus 12, and the like are installed in the hard disk 304. Moreover, a program for causing the display section 320 to perform display and the like based on an analysis result transmitted from the first measurement apparatus 11, a program for analyzing a measurement result transmitted from the second measurement apparatus 12 and for causing the display section 320 to perform display and the like based on the analysis result, and the like are installed in the hard disk 304.

The readout device 305 is implemented by a CD drive, a DVD drive, or the like, and can read out computer programs and data stored in a storage medium. The input section 310 implemented by a mouse and a keyboard is connected to the input/output interface 306. By the user using the input section 310, data is inputted to the information processing apparatus 30. The image output interface 307 is connected to the display section 320 implemented by a display and the like, and outputs video signals corresponding to image data to the display section 320. The display section 320 displays an image based on the inputted video signals. Further, the communication interface 308 allows data transmission/reception between the first measurement apparatus 11, the second measurement apparatus 12, and the host computer 40.

FIG. 6A is a flow chart showing a measurement process performed by the first measurement apparatus 11.

Upon the bar code reader 116 reading out bar code information from the bar code label affixed to a sample container 51 (S101: YES), the CPU 111a of the first measurement apparatus 11 inquires of the information processing apparatus 30 about an order for the first measurement apparatus 11 regarding the sample specified by the bar code information (S102). On the other hand, when bar code information has not been read out (S101: NO), the process is advanced to S108.

Next, the CPU 111a causes the process to wait until receiving the order from the information processing apparatus 30 (S103). Upon receiving the order from the information processing apparatus 30 (S103: YES), the CPU 111a determines, with respect to the sample specified by the bar code information read out in S101, whether it is necessary to perform measurement in the first measurement apparatus 11 (S104). It should be noted that the order includes the type of measurement to be performed by the first measurement apparatus 11, and information of whether measurement is necessary or not. The determination in S104 is performed based on the content of the received order.

When the CPU 111a has determined that it is necessary to perform measurement in the first measurement apparatus 11 (S104: YES), measurement is performed in the first measurement apparatus 11 (S105). That is, the CPU 111a causes the pushing-out mechanism 24 to move the sample rack 50, thereby locating, at the first supply position 26a, the sample container 51 containing the sample for which it has been determined that it is necessary to perform measurement in S104. Then, the CPU 111a causes the nozzle of the first measurement apparatus 11 to aspirate the sample from the sample container 51, and measurement is performed in the first measurement apparatus 11. Subsequently, the CPU 111a analyzes a measurement result of the sample (S106), and transmits the analysis result to the information processing apparatus 30 (S107). On the other hand, when the CPU 111a has determined that it is not necessary to perform measurement in the first measurement apparatus 11 (S104: NO), measurement is not performed for this sample, and the process is advanced to S108.

In this manner, the processes of S101 to S107 are repeatedly performed until the first measurement apparatus 11 is shut down (S108: YES).

FIG. 6B is a flow chart showing a transport process performed by the first measurement apparatus 11. It should be noted that the transport process below is a transport process performed when the sample rack 50 is transported such that a holder of a sample rack 50 located at the first supply position 26a is moved leftward (X-axis positive direction) by the interval d between holders shown in FIG. 3.

The CPU 111a of the first measurement apparatus 11 determines whether a measuring operation for the sample in the sample container 51 located at the first supply position 26a has been completed in the first measurement apparatus 11 (S111).

That is, with respect to the sample in the sample container 51 located at the first supply position 26a, in the case where it has been determined that it is necessary to perform measurement in S104 in FIG. 6A and aspiration has been completed in S105, or in the case where it has been determined that it is not necessary to perform measurement in S104, the CPU 111a determines, in S111 in FIG. 6B, that the measuring operation has been completed. Further, also in the case where no sample container 51 is held in the holder of the sample rack 50 located at the first supply position 26a, it is determined as YES in S111.

When it has been determined that the measuring operation in the first measurement apparatus 11 has been completed (S111: YES), the CPU 111a causes the process to wait until a command most recently received from the second measurement apparatus 12 indicates that transportation is allowed (S112). The command transmitted from the second measurement apparatus 12 will be described later with reference to FIG. 7. On the other hand, when it has been determined that the measuring operation has not been completed in the first measurement apparatus 11 (S111: NO), the process is advanced to S116.

When it has been determined that the command most recently received from the second measurement apparatus 12 indicates that transportation is allowed (S112: YES), the CPU 111a drives the pushing-out mechanism 24, whereby the sample rack 50 is transported leftward (X-axis positive direction) by the interval d between holders. Accordingly, the holder of the sample rack 50 located at the first supply position 26a is moved leftward (X-axis positive direction) by the interval d between holders.

When the sample container 51 is located at the second supply position 26b by being transported in S113 (S114: YES), the CPU 111a transmits, to the second measurement apparatus 12, an aspiration instruction to aspirate the sample in the sample container 51 (S115). On the other hand, when the sample container 51 is not located at the second supply position 26b by being transported in S113 (S114: NO), the process is advanced to S116.

In this manner, the processes of S111 to S115 are repeatedly performed until the first measurement apparatus 11 is shut down (S116: YES).

Figure 7:
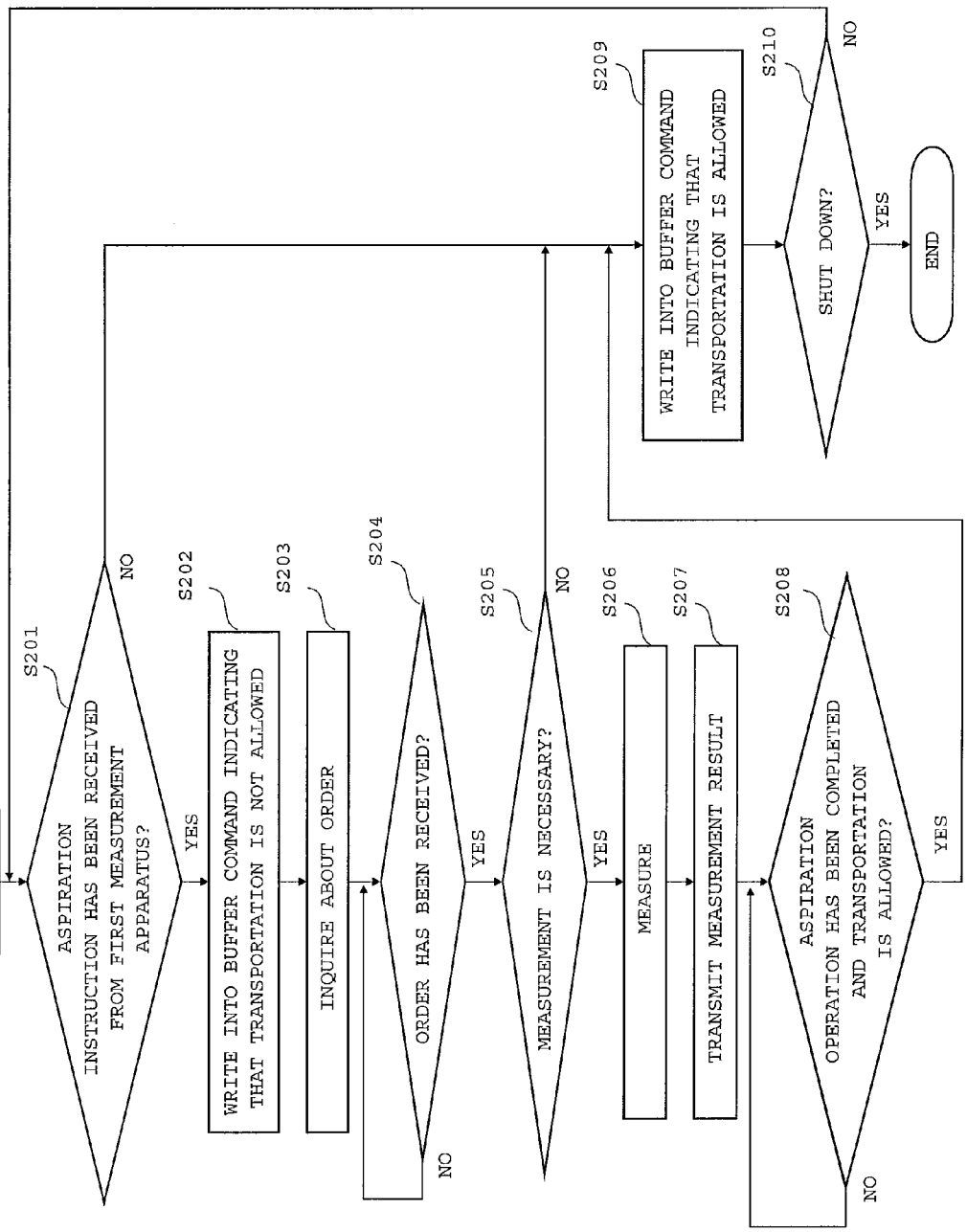
FIG. 7 is a flow chart showing a measurement process performed by the second measurement apparatus according to an embodiment.

FIG. 7 is a flow chart showing a measurement process performed by the second measurement apparatus 12.

Upon receiving the aspiration instruction from the first measurement apparatus 11 (S201: YES), the CPU 121a of the second measurement apparatus 12 writes a command indicating that transportation is not allowed, into a buffer in the storage section 121b of the second measurement apparatus 12 (S202). On the other hand, when not having received the aspiration instruction from the first measurement apparatus 11 (S201: NO), the CPU 121a writes a command indicating that transportation is allowed, into the buffer in the storage section 121b (S209). It should be noted that either one of the command indicating that transportation is allowed and the command indicating that transportation is not allowed is written in the buffer in the storage section 121b.

Next, the CPU 121a inquires of the information processing apparatus 30 about an order for the second measurement apparatus 12 regarding the sample in the sample container 51 located at the second supply position 26b (S203). The CPU 121a causes the process to wait until receiving the order from the information processing apparatus 30 (S204). Upon receiving the order from the information processing apparatus 30 (S204: YES), the CPU 121a determines, with respect to the sample in the sample container 51 located at the second supply position 26b, whether it is necessary to perform measurement in the second measurement apparatus 12 (S205). It should be noted that the order includes the type of measurement to be performed by the second measurement apparatus 12 and information of whether measurement is necessary or not. The determination in S205 is performed based on the content of the received order.

When the CPU 121a has determined that it is necessary to perform measurement in the second measurement apparatus 12 (S205: YES), measurement is performed in the second measurement apparatus 12 (S206). That is, the sample container 51 containing the sample for which it has been determined that measurement is necessary in S205 is subjected to aspiration by the nozzle of the second measurement apparatus 12, and measurement is performed in the second measurement apparatus 12. Subsequently, the CPU 121a transmits the measurement result to the information processing apparatus 30 (S207).

Subsequently, the CPU 121a causes the process to wait until the aspiration operation by the nozzle of the second measurement apparatus 12 is completed for the sample in the sample container 51 located at the second supply position 26b and transportation of the sample rack 50 holding this sample container 51 is allowed (S208). When the aspiration operation for this sample is completed and transportation is allowed (S208: YES), the CPU 121a writes a command indicating that transportation is allowed, into the buffer in the storage section 121b (S209).

Also when it has been determined that it is not necessary to perform measurement in the second measurement apparatus 12 for the sample in the sample container 51 located at the second supply position 26b (S205: NO), the CPU 121a writes a command indicating that transportation is allowed, into the buffer in the storage section 121b (S209).

In this manner, the processes of S201 to S209 are repeatedly performed until the second measurement apparatus 12 is shut down (S210: YES).

Figure 8B:
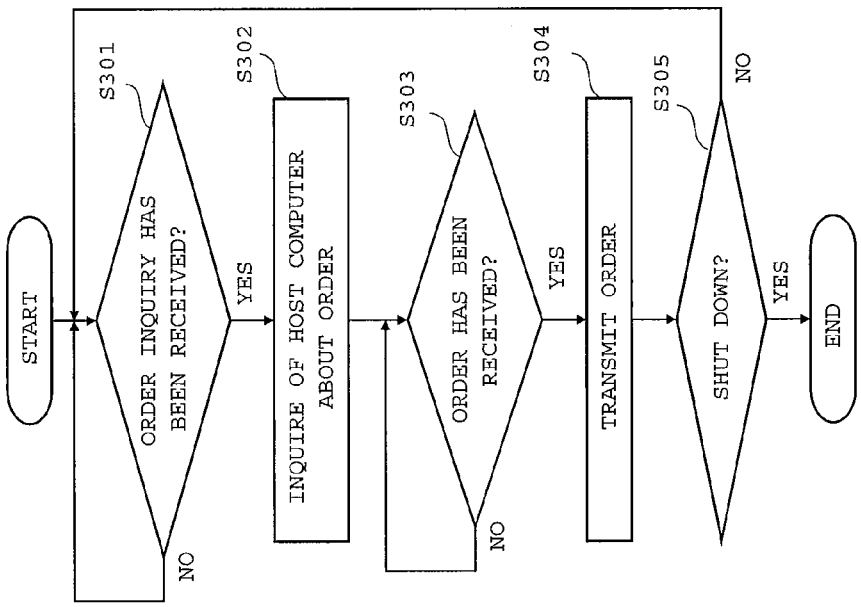
FIGS. 8A and 8B show flow charts respectively showing a command transmitting process performed by the second measurement apparatus and an order process performed by the information processing apparatus according to an embodiment.
Figure 8A:
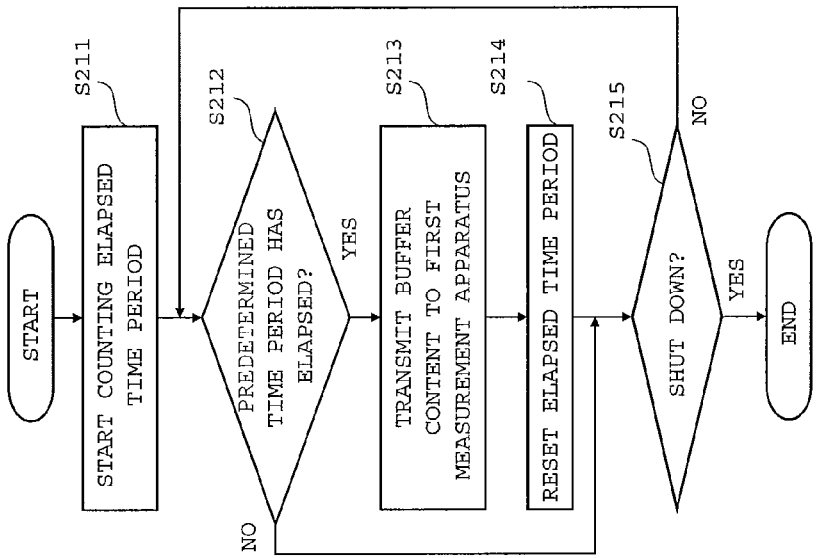

FIG. 8A is a flow chart showing a command transmitting process performed by the second measurement apparatus 12.

First, the CPU 121a of the second measurement apparatus 12 starts counting an elapsed time period (S211). Next, based on the count of the elapsed time period, the CPU 121a determines whether a predetermined time period has elapsed (S212). When the predetermined time period has elapsed (S212: YES), the CPU 121a transmits to the first measurement apparatus 11 the command stored in the storage section 121b of the second measurement apparatus 12 (S213), and resets the elapsed time period (S214).

In this manner, the processes of S212 to S214 are repeatedly performed until the second measurement apparatus 12 is shut down (S215: YES). Accordingly, the command stored in the storage section 121b of the second measurement apparatus 12 is transmitted to the first measurement apparatus 11 every predetermined time period.

FIG. 8B is a flow chart showing an order process performed by the information processing apparatus 30.

The CPU 301 of the information processing apparatus 30 causes the process to wait until receiving an order inquiry from the first measurement apparatus 11 or the second measurement apparatus 12 (S301). Upon receiving an order inquiry (S301: YES), the CPU 301 inquires of the host computer 40 about an order, based on this order inquiry (S302). The host computer 40 determines an order in accordance with the order inquiry.

The CPU 301 causes the process to wait until receiving the order from the host computer 40 (S303) as a result of the order inquiry performed in S302. Upon receiving the order (S303: YES), the CPU 301 transmits the received order to the first measurement apparatus 11 or the second measurement apparatus 12 from which the original order inquiry was received (S304).

In this manner, the processes of S301 to S304 are repeatedly performed until the information processing apparatus 30 is shut down (S305: YES). It should be noted that, when order inquiries are received from the first measurement apparatus 11 and the second measurement apparatus 12, the order processes are performed in parallel.

FIG. 9 shows flow charts respectively showing display processes performed by the information processing apparatus 30. FIG. 9A shows a process of displaying an analysis result obtained by the first measurement apparatus 11, and FIG. 9B is a process of displaying an analysis result obtained by the second measurement apparatus 12.

With reference to FIG. 9A, upon receiving an analysis result from the first measurement apparatus 11 (S311: YES), the CPU 301 of the information processing apparatus 30 causes the display section 320 of the information processing apparatus 30 to display the analysis result (S312). Subsequently, the CPU 301 transmits the analysis result to the host computer 40 (S313).

In this manner, the processes of S311 to S313 are repeatedly performed until the information processing apparatus 30 is shut down (S314: YES).

Next, with reference to FIG. 9B, upon receiving a measurement result from the second measurement apparatus 12 (S321: YES), the CPU 301 of the information processing apparatus 30 analyzes the measurement result (S322) and causes the display section 320 of the information processing apparatus 30 to display the analysis result (S323). Subsequently, the CPU 301 transmits the analysis result to the host computer 40 (S324).

In this manner, the processes of S321 to S324 are repeatedly performed until the information processing apparatus 30 is shut down (S325: YES).

FIG. 10A is a flow chart showing an order determination process performed by the host computer 40.

Upon receiving an analysis result obtained by the first measurement apparatus 11 transmitted from the information processing apparatus 30 in S313 in FIG. 9A (S401: YES), the CPU 401a of the host computer 40 stores the analysis result in the storage section 401b (S402). Subsequently, the CPU 401a determines an order for the second measurement apparatus 12, based on the analysis result obtained by the first measurement apparatus 11 received in S401 and the measurement requiring criteria stored in advance in the storage section 401b (S403). For example, in the case where, among analysis results of a sample obtained by the first measurement apparatus 11, a value of a specific type of measurement item exceeds a predetermined value, the CPU 401a determines an order including a content that measurement of the sample needs to be performed in the second measurement apparatus 12 and the type of measurement to be performed. The determined order for the second measurement apparatus 12 is stored in the storage section 401b (S404).

In this manner, the processes of S401 to S404 are repeatedly performed until the host computer 40 is shut down (S405: YES).

It should be noted that upon receiving the analysis result obtained by the second measurement apparatus 12 transmitted from the information processing apparatus 30 in S324 in FIG. 9B, the CPU 401a stores the analysis result in the storage section 401b.

FIG. 10B is a flow chart showing an order reply process performed by the host computer 40.

Upon receiving an order inquiry transmitted from the information processing apparatus 30 in S302 in FIG. 8B (S411: YES), the CPU 401a of the host computer 40 transmits the order for the first measurement apparatus 11 or the second measurement apparatus 12 stored in the storage section 401b, to the information processing apparatus 30 (S412).

In this manner, the processes of S411 to S412 are repeatedly performed until the host computer 40 is shut down (S413: YES).

It should be noted that the order transmitted to the information processing apparatus 30 in S412 is transmitted to the first measurement apparatus 11 or the second measurement apparatus 12 in S304 in FIG. 8B. Based on the order transmitted in this manner, the first measurement apparatus 11 or the second measurement apparatus 12 determines whether measurement of the sample is necessary or not, in S104 in FIG. 6A or S205 in FIG. 7, respectively.

As described above, according to the present embodiment, the distance between the first supply position 26a and the second supply position 26b is set to be shorter than or equal to the distance between the sample container 51 held in the holder at the left end of the sample rack 50 and the sample container 51 held in the holder at the right end thereof. Further, the interval between the first supply position 26a and the second supply position 26b is set to a multiple of the distance d between adjacent sample containers 51 held in the sample rack 50. Accordingly, it is possible to concurrently locate the sample containers 51 held in two different holders in one sample rack 50, at the first supply position 26a and the second supply position 26b, respectively. Therefore, it is possible to efficiently perform processing of samples.

Further, according to the present embodiment, in FIG. 7, from when the second measurement apparatus 12 has received an aspiration instruction (S201: YES), at least until it is determined whether measurement needs to be performed by the second measurement apparatus 12 (S205), a command indicating that transportation is not allowed is written in the buffer in the storage section 121b. Accordingly, among the samples located at the second supply position 26b, a sample which needs to be measured by the second measurement apparatus 12 can be prevented from being transported to the downstream side without being aspirated.

In the present embodiment, in FIG. 7, from when an order inquiry is issued to the information processing apparatus 30 (S203) until the second measurement apparatus 12 receives an order, the process is caused to wait (S204). If the time period of the waiting process in S204 becomes long, supply of a subsequent sample located at the first supply position 26a to the first measurement apparatus 11 is stagnated since a sample rack 50 cannot be transported in the downstream direction (the X-axis positive direction in FIG. 2) during such a waiting process. When the waiting time period in S204 poses a problem, the distance between the first supply position 26a and the second supply position 26b in the present embodiment shown in FIG. 2 may be adjusted so as to be longer as appropriate.

FIG. 11 illustrates how to set the distance between the first supply position 26a and the second supply position 26b.

FIG. 11A is a time chart schematically showing the flow from when a sample is located at the first supply position 26a to when aspiration of the sample is performed by the second measurement apparatus 12. As shown in FIG. 11A, the time period from when aspiration by the first measurement apparatus 11 is started till an order for the second measurement apparatus 12 is determined by the host computer 40 is Ts.

FIG. 11B is a plan view schematically showing the flow from when a sample container 51 held in the holder at the left end of the sample rack 50 is located at the first supply position 26a to when it is located at the second supply position 26b.

After the sample container 51 is located at the second supply position 26b, an order inquiry for the second measurement apparatus 12 is performed. If the order for the second measurement apparatus 12 has not been determined by the host computer 40 at the time of the order inquiry, a waiting time period for the sample container 51 at the second supply position 26b becomes long.

Here, it is assumed that no sample containers 51 are held in holders other than the holder at the left end of the sample rack 50. When a sample container 51 is held only in the holder at the left end of the sample rack 50 as in this case, the time period T0 from when aspiration by the first measurement apparatus 11 is started at the first supply position 26a till the sample container 51 is located at the second supply position 26b becomes shortest.

Here, it is sufficient that the distance between the first supply position 26a and the second supply position 26b is set such that the time period Ts is shorter than the time period T0. That is, it is sufficient that the distance between the first supply position 26a and the second supply position 26b is set to be longer than or equal to the distance by which the sample container 51 is transported during the time period Ts after the sample in the sample container 51 is aspirated at the first supply position 26a. Also in this case, as shown in FIG. 3, the distance between the first supply position 26a and the second supply position 26b is a multiple of d. This shortens the waiting time period at the second supply position 26b, and thus, processing of the sample at the second supply position 26b can be performed smoothly and speedily. Thus, it is possible to speedily supply the subsequent sample located at the first supply position 26a to the first measurement apparatus 11.

An embodiment of the present invention has been described. However, the present invention is not limited to the above embodiment.

For example, in the above embodiment, a subject to be measured is exemplified by urine, but a subject to be measured may be blood. That is, the present invention can also be applied to a sample analyzer which tests blood, and further, the present invention can be applied to a clinical sample analyzer which tests other clinical samples.

Further, in the above embodiment, the samples are aspirated from the sample containers 51 located at the first supply position 26a and the second supply position 26b, respectively. However, the present invention is not limited thereto. The sample containers 51 located at the first supply position 26a and the second supply position 26b are taken into the first measurement apparatus 11 and the second measurement apparatus 12, respectively, and the samples may be aspirated from the sample containers 51 in the respective apparatuses.

Further, in the above embodiment, the distance between the first supply position 26a and the second supply position 26b is set to be shorter than or equal to the distance between the sample container 51 held in the holder at the left end of the sample rack 50 and the sample container 51 held in the holder at the right end thereof. However, the present invention is not limited thereto. The distance between the first supply position 26a and the second supply position 26b may be set to be longer than the distance between the sample container 51 held in the holder at the left end of the sample rack 50 and the sample container 51 held in the holder at the right end thereof. In this case, the sample rack 50 is configured such that, when two sample racks 50 are arranged next to each other in the connection region 21c shown in FIG. 2, the distance between the sample container 51 held in the holder at the right end of the downstream sample rack 50 and the sample container 51 held in the holder at the left end of the upstream sample rack 50 is a multiple of d. Further, in this case, the transporting apparatus 20 is configured to transport the upstream sample rack 50, whereby the upstream sample rack 50 pushes the downstream sample rack 50, whereby both sample racks 50 are transported.

FIG. 12 shows modifications of the distance between the first supply position 26a and the second supply position 26b.

Figure 12A:
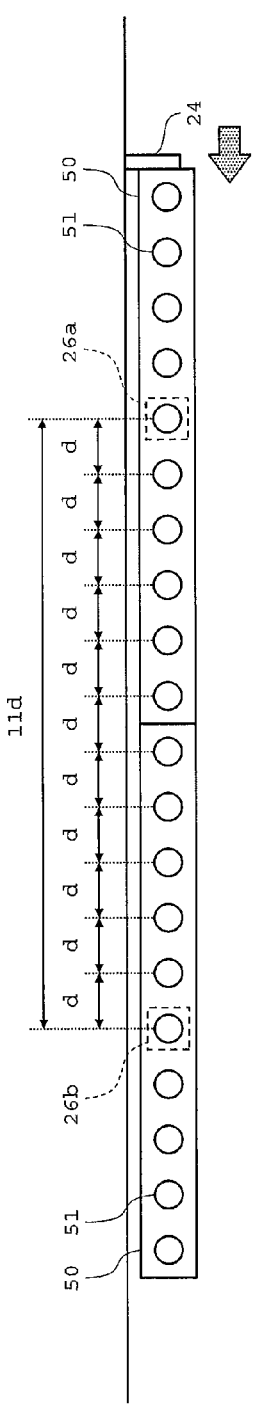
FIGS. 12A-12C show modifications of the distance between the first supply position and the second supply position according to an embodiment.
Figure 12B:
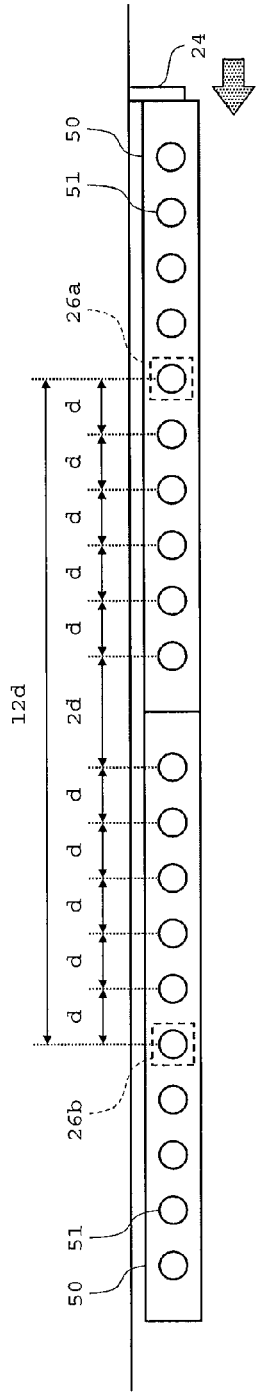
Figure 12C:
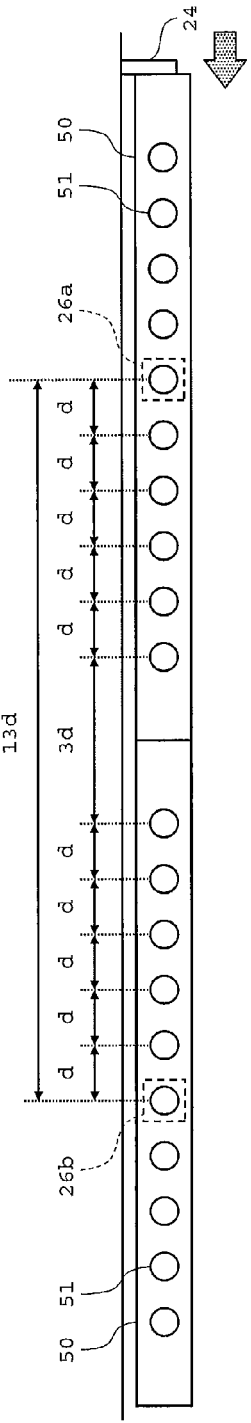

In FIG. 12A to 12C, the distances between the first supply position 26a and the second supply position 26b are 11*d*, 12*d*, and 13*d*, respectively. Moreover, in FIG. 12A to 12C, the distances between the sample container 51 held in the holder at the right end of the downstream sample rack 50 and the sample container 51 held in the holder at the left end of the upstream sample rack 50 are d, 2*d*, and 3*d*, respectively. Further, as shown in FIG. 12A to 12C, by the right-end side face of the upstream sample rack 50 being pushed by the pushing-out mechanism 24, the upstream sample rack 50 pushes the downstream sample rack 50, whereby these two adjacent sample racks 50 are concurrently transported in the downstream direction.

As a result, although samples held in different holders of one sample rack 50 are not concurrently located at the first supply position 26a and the second supply position 26b, respectively, samples held in holders of adjacent sample racks 50 are concurrently located at the first supply position 26a and the second supply position 26b, respectively. Accordingly, it is possible to simultaneously process two samples as in the above embodiment, and thus it is possible to efficiently perform processing of samples.

Further, in the above embodiment, ten holders are formed in the sample rack 50 so as to hold ten sample containers 51. However, the present invention is not limited thereto. Five holders may be formed in a sample rack, so as to hold not ten but five, for example, sample containers 51.

Further, in the above embodiment, the order for the second measurement apparatus 12 is determined by the host computer 40, based on an analysis result obtained by the first measurement apparatus 11. Moreover, the order for the first measurement apparatus 11 and the order for the second measurement apparatus 12 are stored in the storage section 401*b* of the host computer 40. However, these processes may be performed by the information processing apparatus 30.

Figure 13:
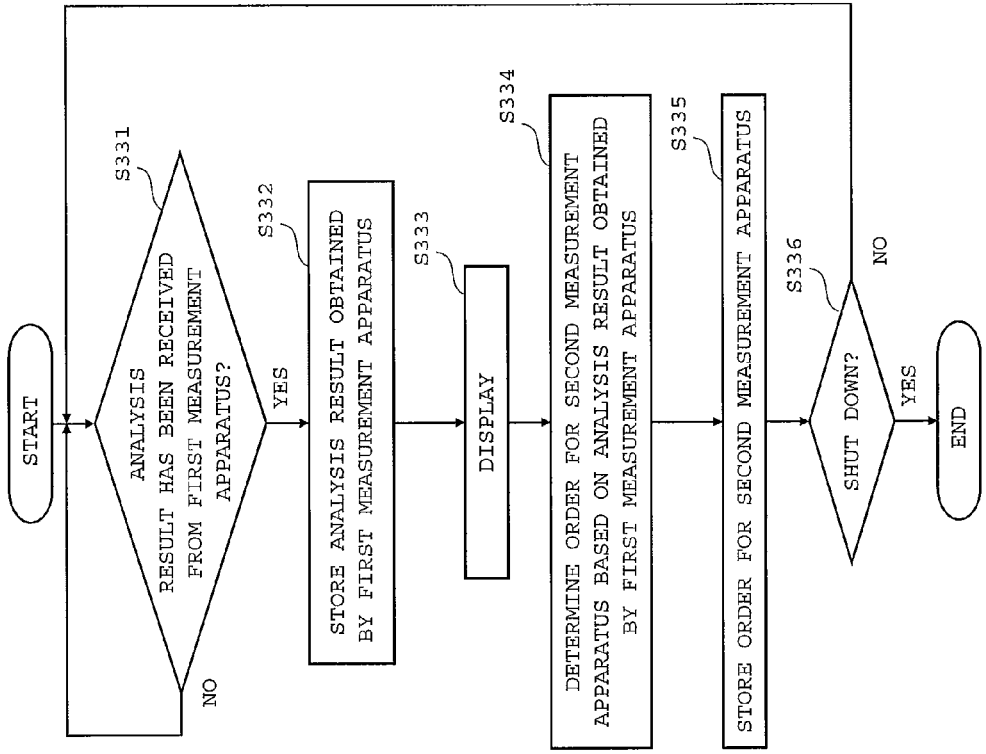
FIG. 13 is a flow chart showing a display process and an order determination process performed by the information processing apparatus according to a modification of an embodiment.

FIG. 13 is a flow chart showing a display process and an order determination process performed by the information processing apparatus 30. Such processes are performed instead of the process shown in FIG. 9A of the above embodiment.

Upon receiving an analysis result from the first measurement apparatus 11 (S331: YES), the CPU 301 of the information processing apparatus 30 stores the analysis result in the hard disk 304 (S332), and causes the display section 320 to display the analysis result (S312). Subsequently, the CPU 301 determines an order for the second measurement apparatus 12 based on the analysis result obtained by the first measurement apparatus 11 which has been received in S331 and the measurement requiring criteria stored in advance in the hard disk 304 (S334). The determined order for the second measurement apparatus 12 is stored in the hard disk 304 (S335).

In this manner, the processes of S331 to S335 are repeatedly performed until the information processing apparatus 30 is shut down (S336: YES).

It should be noted that, when the CPU 301 of the information processing apparatus 30 has received a measurement result from the second measurement apparatus 12, the CPU 301 analyzes the measurement result, stores the resultant analysis result in the hard disk 304, and causes the display section 320 to display the analysis result. When the CPU 301 of the information processing apparatus 30 has received an order inquiry from the first measurement apparatus 11 or the second measurement apparatus 12, the CPU 301 transmits the order for the first measurement apparatus 11 or the second measurement apparatus 12 stored in the hard disk 304 to the corresponding apparatus, in accordance with the process steps as in the FIG. 10B.

In addition to the above, various modifications can be made as appropriate without departing from the scope of the technical idea defined by the claims.

What is claimed is:

1. A urine sample analyzer which transports a rack holding a plurality of sample containers and analyzes samples, the sample analyzer comprising:
    a urine qualitative measurement apparatus which measures samples;
    a urinary sediment measurement apparatus which is arranged downstream, in a transport direction, from the urine qualitative measurement apparatus, and which measures urine samples;
    a transporting apparatus which transports samples to a first supply position for supplying a sample to the urine qualitative measurement apparatus, and to a second supply position for supplying a sample to the urinary sediment measurement apparatus, and
    a controller which determines, based on a measurement result obtained by the urine qualitative measurement apparatus whether measurement by the urinary sediment measurement apparatus is necessary, wherein
    the transporting apparatus linearly transports a rack from the first supply position to the second supply position, and
    a distance between the first supply position and the second supply position is a multiple of a distance between adjacent sample containers held in the rack, and
    until the controller determines whether the measurement by the urinary sediment measurement apparatus is necessary, the controller is configured to control the transporting apparatus not to transport a sample for which the determination is made, to downstream from the second supply position.

2. The urine sample analyzer according to claim 1, wherein the transporting apparatus transports one sample to the first supply position and transports another sample to the second supply position, by a common transport mechanism.

3. The urine sample analyzer according to claim 1, wherein the distance between the first supply position and the second supply position is shorter than or equal to a distance from a sample container held in one rack at one end thereof to a sample container held in the rack at the other end thereof.

4. The urine sample analyzer according to claim 1, wherein the urine qualitative measurement apparatus is configured to aspirate a sample present at the first supply position, and the urinary sediment measurement apparatus is configured to aspirate a sample present at the second supply position.

5. The urine sample analyzer according to claim 1, wherein the controller configured to control the urine qualitative measurement apparatus to aspirate a sample from the sample containers located at the first supply position and to control the urinary sediment measurement apparatus to aspirate a sample from the sample containers located at the second supply position.

6. The urine sample analyzer according to claim 1, wherein the controller configured to control the urine qualitative measurement apparatus to take the sample containers located at the first supply position into the urine qualitative measurement apparatus and as rate the samples from the sample containers in the urine qualitative measurement apparatus; and the controller configured to control the urine sediment measurement apparatus to take the second supply position into the urinary sediment measurement apparatus and aspirate the samples from the sample containers in the urinary sediment measurement apparatus.

7. The urine sample analyzer according to claim 1, wherein the transporting apparatus transports two racks so that a sample held in one rack is located at the first supply position and a sample held in the other rack is located at the second supply position.

8. A urine sample analysis system comprising:

a sample analyzer which transports a rack holding a plurality of sample containers and analyzes samples; and a computer communicable to the sample analyzer, wherein the sample analyzer comprises:

a urine qualitative measurement apparatus which measures samples;

a urinary sediment measurement apparatus which is arranged downstream, in a transport direction, from the urine qualitative measurement apparatus, and which measures samples;

a transporting apparatus which transports samples to a first supply position for supplying a sample to the urine qualitative measurement apparatus, and to a second supply position for supplying a sample to the urinary sediment measurement apparatus, a controller, wherein the transporting apparatus linearly transports a rack from the first supply position to the second supply position, a distance between the first supply position the second supply position is a multiple of a distance between adjacent sample containers held in the rack, the computer comprises a determination section which determines, based on a measurement result obtained by the urine qualitative measurement apparatus, whether measurement by the urinary sediment measurement apparatus is necessary, and until the controller determines whether the measurement by the urinary sediment measurement apparatus is necessary, the controller is configured to control the transporting apparatus not to transport a sample for which the determination is made, to downstream from the second supply position.

9. The urine sample analysis system according to claim 8, wherein the transporting apparatus transports one sample to the first supply position and transports another sample to the second supply position, by a common transport mechanism.

10. The urine sample analysis system according to claim 8, wherein the urine qualitative measurement apparatus is configured to aspirate a sample present at the first supply position, and the urinary sediment measurement apparatus is configured to aspirate a sample present at the second supply position.

11. The urine sample analysis system according to claim 8, wherein the controller configured to control the urine qualitative measurement apparatus to aspirate a sample from the sample containers located at the first supply position and to control the urinary sediment measurement apparatus to aspirate a sample from the sample containers located at the second supply position.

12. The urine sample analysis system according to claim 8, wherein the controller is configured to control the urine qualitative measurement apparatus to take the sample containers located at the first supply position into the urine qualitative measurement apparatus and aspirate the samples from the sample containers in the urine qualitative measurement apparatus; and the controller is configured to control the urinary sediment measurement apparatus to take the sample containers located at the second supply position into the urinary sediment measurement apparatus and aspirate the samples from the sample containers in the urinary sediment measurement apparatus.

13. The urine sample analysis system according to claim 8, wherein the transporting apparatus transports two racks so that a sample held in one rack is located at the first supply position and a sample held in the other rack is located at the second supply position.

\* \* \* \* \*

UNITED STATES PATENT AND TRADEMARK OFFICE
CERTIFICATE OF CORRECTION

Page 1 of 1

PATENT NO. : 8,641,988 B2
APPLICATION NO. : 13/629081
DATED : February 4, 2014
INVENTOR(S) : Toru Mizumoto et al.

It is certified that error appears in the above-identified patent and that said Letters Patent is hereby corrected as shown below:

In the Claims

In column 17, claim 6, line 4, after "configured to control the" replace "urine" with --urinary--.

Signed and Sealed this
Third Day of June, 2014

Michelle K. Lee
*Deputy Director of the United States Patent and Trademark Office*

UNITED STATES PATENT AND TRADEMARK OFFICE
CERTIFICATE OF CORRECTION

| | |
|---|---|
| PATENT NO. | : 8,641,988 B2 |
| APPLICATION NO. | : 13/629081 |
| DATED | : February 4, 2014 |
| INVENTOR(S) | : Toru Mizumoto et al. |

It is certified that error appears in the above-identified patent and that said Letters Patent is hereby corrected as shown below:

On the Title Page

Item (73), immediately after "Kobe (JP)" insert --; Arkray, Inc., Kyoto (JP)--.

Signed and Sealed this
Twenty-first Day of April, 2015

Michelle K. Lee
*Director of the United States Patent and Trademark Office*